United States Patent [19]
Adams et al.

[11] Patent Number: 5,997,481
[45] Date of Patent: Dec. 7, 1999

[54] PROBE COVER WITH DEFORMABLE MEMBRANE GEL RESERVOIR

[75] Inventors: Wanda F. Adams; Joe B. Massey, both of Atlanta, Ga.

[73] Assignee: Ultra Sound Probe Covers, LLC, Atlanta, Ga.

[21] Appl. No.: 09/024,091

[22] Filed: Feb. 17, 1998

[51] Int. Cl.[6] .................................................. A61B 8/14
[52] U.S. Cl. ........................................................... 600/459
[58] Field of Search .................................. 600/437, 459, 600/461, 462; 73/588, 644

[56] References Cited

U.S. PATENT DOCUMENTS

| | | | |
|---|---|---|---|
| 4,593,699 | 6/1986 | Poncy et al. | 128/660 |
| 4,603,701 | 8/1986 | Chen | 128/660 |
| 4,722,346 | 2/1988 | Chen | 128/660 |
| 4,815,470 | 3/1989 | Curtis et al. | 128/662.03 |
| 4,844,080 | 7/1989 | Frass et al. | 600/437 |
| 5,002,059 | 3/1991 | Crowley et al. | 128/662.06 |
| 5,078,149 | 1/1992 | Katsumata et al. | 128/662.03 |
| 5,335,663 | 8/1994 | Oakley et al. | 128/662 |
| 5,355,886 | 10/1994 | Losa Dominguez et al. | 128/660.01 |
| 5,437,283 | 8/1995 | Ranalletta et al. | 128/662.06 |
| 5,469,853 | 11/1995 | Law et al. | 128/662.06 |
| 5,494,038 | 2/1996 | Wang et al. | 600/459 |

OTHER PUBLICATIONS

Study Guide, Chapter 7, Transvaginal Sonography, Transvaginal Probe Covers, pp. 323–324 (Author & Date Unknown).

Advertisement, Eclipse Probe Cover—Parker Laboratories, Inc. (Date Unknown).

Page Probe Covers and Biopsy Needles (Date & Source unknown).

CIVCO Medical Instruments Brochure (Nov./Dec. 1996).

Swemed Lab. Sterile Ultrasound transducer cover (Date unknown).

*Primary Examiner*—Francis J. Jaworski
*Assistant Examiner*—Ali M. Imam
*Attorney, Agent, or Firm*—Needle & Rosenberg, P.C.

[57] ABSTRACT

A probe cover for an ultrasonic imaging probe, the cover including a reservoir for containing a quantity of ultrasonically transmissive gel. The reservoir is formed by a deformable membrane having a passage allowing a portion of the gel to flow through the membrane. The membrane deforms upon insertion of the probe into the cover, causing some of the gel to pass through the passage, into contact with the transducer portion of the probe. The remainder of the gel is retained in place within the reservoir to provide ultrasonic contact with the target body to be imaged by the probe. Tie elements can be provided for securing the cover to the probe.

25 Claims, 4 Drawing Sheets

PROBE COVER WITH DEFORMABLE MEMBRANE GEL RESERVOIR

BACKGROUND OF THE INVENTION

1. Field of the Invention

This invention relates generally to a cover for a medical ultrasonic imaging probe. More particularly, this invention relates to a probe cover having a reservoir for containing a quantity of ultrasonic imaging gel, the reservoir bounded by a deformable membrane which is flexible by contact with the probe upon insertion into the cover. Deformation of the membrane expels a portion of the gel through the membrane, into contact with the probe. The remainder of the gel stays in position within the reservoir, thereby assuring constant ultrasonic contact between the probe and the cover.

2. Description of Related Art

Ultrasonic imaging is used in the medical field for a number of applications requiring non-invasive observation of internal anatomical tissue and structures. One common application of ultrasonic imaging is to monitor the development of a fetus during pregnancy. Ultrasonic imaging is also frequently used in pre-surgical diagnosis of internal organs, and to locate tissue and organs during laparoscopic surgery.

An ultrasonic probe having one or more transducer elements, or crystals, is typically used to transmit and receive ultrasonic signals directed to the tissue of interest. The signals are processed to generate a visual display, commonly on a video monitor. Due to the expense of the probes, it is necessary that the probes be reused for examining many patients. The construction of the probes, however, renders them difficult, if not impossible, to effectively sterilize between successive uses. Therefore, a disposable, sterile probe cover or sheath is typically placed over the probe prior to use with each patient, and discarded after the examination is complete.

In order to achieve good ultrasonic imaging, it is necessary that ultrasonic contact or coupling be maintained between the probe and the target body or tissue to be observed. The use of a probe cover can adversely affect this ultrasonic contact if air pockets or other non-ultrasonically transmissive voids come between the cover and the probe. In order to maintain ultrasonic contact between the probe and the cover, ultrasonically transmissive gel is placed between the probe and the cover. It has been found that application of too much or too little of the gel between the probe and the cover will cause ultrasonic reverberation artifacts which degrade the image quality. Therefore, with known covers, it is necessary to closely control the quantity of gel applied.

Several types of probe covers are presently available. One variety is a thin-walled, flexible, tightly-fitting condom made of an elastomeric material such as latex rubber. In use, a quantity of ultrasonic gel is placed loosely inside the tip of the condom, and the condom is then stretched over the probe and secured with rubber bands or plastic clips. Several disadvantages have been found to result from the use of this type of probe cover. First, as described above, the quantity of gel introduced into the cover must be closely controlled to insure good imaging. This is time consuming and requires some amount of guesswork. Another disadvantage of this type of probe cover is that the gel is often displaced out of the tip area during the installation of the cover onto the probe, and/or during use. For example, the gel often slides down the sides of the probe as the cover is stretched over the probe or as the probe is moved along the outer surface of the target body, leaving an insufficient quantity of gel around the tip of the probe. Problems are also encountered with this type of probe cover due to the clips or rubber bands used to secure the cover to the probe. Rubber bands tend to break while scanning, allowing the probe cover to shift on the probe, thereby causing imaging quality to deteriorate. The outwardly-extending tips of the plastic or metal clips sometimes used to secure the covers often cause pain or discomfort to the patient. Still another disadvantage of this type of probe cover is that their manufacturers often apply a powder such as talc to the condoms to prevent their sticking together. These powders may contain embryotoxic compounds, rendering the use of these covers incompatible with transvaginal egg retrieval procedures.

Another type of known probe cover is a loose-fitting, thin-walled, sleeve made of flexible material such as polyethylene. These covers are typically installed by placing a quantity of ultrasonic gel either on the tip of the probe or in the tip end of the cover, inserting the probe into the cover, and securing the cover to the probe with clips or rubber bands. This type of cover suffers the same types of disadvantages as described above. In addition, the loose fitting nature of these covers lends to the possibility of the shifting of the cover on the probe and/or the shifting of the gel within the cover during installation and use.

U.S. Pat. No. 5,335,663 to Oakley, et al. discloses a sheath for covering an ultrasonic probe which sheath includes a chamber at its tip for containing an ultrasonically transmissive medium. The chamber is described as partitioned from the remainder of the sheath's interior by a thin membrane which is ruptured when the probe is inserted into the sheath. The Oakley, et al. sheath may address the disadvantage discussed above, regarding the necessity of accurately measuring the proper quantity of ultrasonic gel applied between the probe and the cover. Also, at least to some extent, the Oakley, et al. sheath may successfully retain the gel in the tip region of the sheath during installation of the sheath onto the probe. Several known disadvantages, however, remain unaddressed by the Oakley, et al. sheath. For instance, once the probe ruptures the membrane, the gel is no longer constrained in place in the region of the probe tip, and may be displaced by further use of the probe. This can result in an insufficient amount of gel in the area of the probe tip for good ultrasonic imaging, and can allow a loss of ultrasonic contact between the cover and the probe. Additionally, the Oakley, et al. sheath is described as rigid and attached to the probe by the latching of a protrusion and a corresponding recess. This requires the sheath to be dimensioned for a close fit to a particular probe, thereby sacrificing the ability to provide a cover for general application to a number of probes having different external geometries. Rigid sheaths are also more expensive than flexible sheaths, and can interfere with the use of the probe in many applications. Oakley, et al. also does not address the above-described disadvantages of known devices for securing flexible-walled probe covers to a probe.

Thus, it can be seen that a need exists for a probe cover which eliminates the necessity for measuring the quantity of ultrasonic gel applied, and assures that the proper quantity of gel necessary for good ultrasonic imaging is utilized. A further need exists for a probe cover which maintains the proper quantity of gel in position over the transducer portion of the probe throughout the installation and use of the cover, and which maintains ultrasonic contact between the probe and the cover and between the cover and the target body. The need further exists for a probe cover that can be securely attached to a probe, reducing or eliminating the possibility that the cover will shift on the probe during installation and use, and including secure attachment means that will not cause discomfort to the patient. It is to the provision of such a device that the present invention is primarily directed.

SUMMARY OF THE INVENTION

The above-noted disadvantages of the prior art are overcome by the present invention, which in one aspect is a probe cover for covering at least a portion of an ultrasonic imaging probe. The probe cover includes a hollow body portion having interior and exterior surfaces, the interior surface defining a chamber for receiving at least a portion of the ultrasonic imaging probe. An opening in the hollow body portion communicates with the chamber and allows insertion of the probe. The probe cover also has a deformable membrane within the hollow body portion, preferably attached to the interior surface adjacent the end of the chamber opposite the opening. This deformable membrane defines a pocket or reservoir for containing a quantity of ultrasonically transmissive medium, such as ultrasonic imaging gel. The deformable membrane has at least one passage or vent therethrough which permits a portion of the ultrasonically transmissive medium to flow through the membrane upon its deformation.

Another aspect of the present invention provides a probe cover for covering at least the transducer portion of an ultrasonic imaging probe. The probe cover includes a flexible sheath having an interior surface and an exterior surface. The sheath's interior surface defines a chamber for receiving at least the transducer portion of the ultrasonic imaging probe. A reservoir is provided in the sheath, adjacent the chamber, for retaining a quantity of ultrasonically transmissive medium in ultrasonic contact with the transducer portion of the ultrasonic imaging probe. This reservoir may be formed from a deformable membrane which has at least one passage for allowing the ultrasonically transmissive medium to flow therethrough, between the reservoir and the chamber. Upon contact with the transducer portion of the ultrasonic imaging probe, the deformable membrane deforms and compresses the reservoir, causing some of the ultrasonically transmissive medium to flow through the at least one passage, into the chamber and into contact with the probe.

The probe cover of the present invention can further include a securing means such as a tie element for attaching the probe cover to the probe. The tie element preferably has two separate tie elements each attached at one end to the exterior of the probe cover's wall, or alternatively a single tie element having a middle portion attached to the wall and two free ends extending therefrom. The tie elements can be wrapped around the probe cover and tied off to secure the probe cover in place on the probe. The tie elements are preferably formed from the same flexible material as the wall portion of the probe cover. Because the tie elements are attached to the wall of the probe cover, they are not susceptible to breakage and dislodgement as are the rubber bands previously used to secure probe covers. Also, because of their flexible material of construction, they do not cause discomfort to patients as do the clips used in the past.

Another aspect of the present invention is a method of covering an ultrasonic imaging probe with a flexible probe cover. The probe cover is substantially as described above, having a deformable membrane defining a reservoir for containing a quantity of ultrasonically transmissive medium. The method is carried out by inserting at least a portion of the ultrasonic imaging probe into the flexible probe cover, contacting the ultrasonic imaging probe with the deformable membrane, and deforming the deformable membrane into a deformed position due to the contact with the ultrasonic imaging probe to cause a portion of the quantity of ultrasonically transmissive medium to flow from the reservoir through the at least one passage in the deformable membrane into ultrasonic contact with the ultrasonic imaging probe, under the influence of the deformation of the deformable membrane.

As described in greater detail herein, the probe cover of the present invention, and its method of use, provide several advantages over known probe covers and their methods of use. For example, the probe cover and method of the present invention eliminate the necessity for measuring the quantity of ultrasonic gel applied, and assure that the proper quantity of gel necessary for good ultrasonic imaging is utilized. The probe cover and method of the present invention also maintain the proper quantity of gel in position over the transducer portion of the probe throughout the installation and use of the cover, and maintain ultrasonic contact between the probe and the cover and between the cover and the target body. Unlike known probe covers having a breakable membrane, the deformable membrane of the present invention stays intact and does not allow the gel to be displaced away from the transducer portion of the probe during the examination. The probe cover and method of the present invention also provide for secure attachment of the probe cover and the probe, thereby reducing or eliminating the possibility that the cover will shift on the probe during installation and use, as well as reducing or eliminating discomfort to the patient.

These and other advantages will become apparent from the following description of the preferred embodiment taken in conjunction with the following drawings, although variations and modifications may be effected without departing from the spirit and scope of the novel concepts of the disclosure.

DETAILED DESCRIPTION OF THE INVENTION

Figure 1:
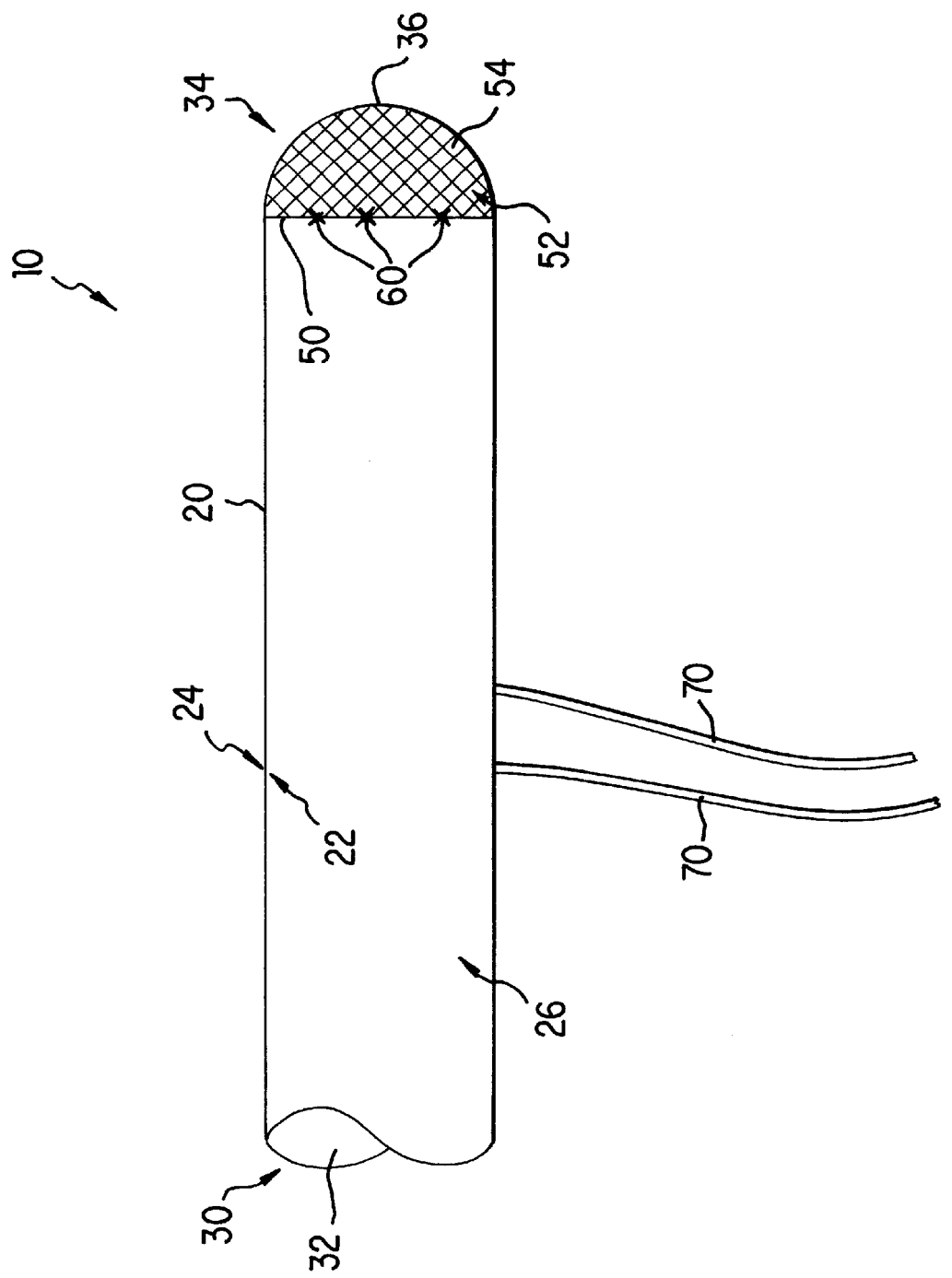
FIG. 1 is a side view, in partial cross-section, of a probe cover according to the present invention.

Referring now in detail to the drawing figures, wherein like reference numbers indicate like parts throughout, the preferred embodiments of the present invention will now be described. As used in the description herein and throughout the claims that follow, "a," "an," and "the" includes plural reference unless the context clearly dictates otherwise. Also, as used in the description herein and throughout the claims that follow, the meaning of "in" includes "in" and "on" unless the context clearly dictates otherwise.

Figure 2:
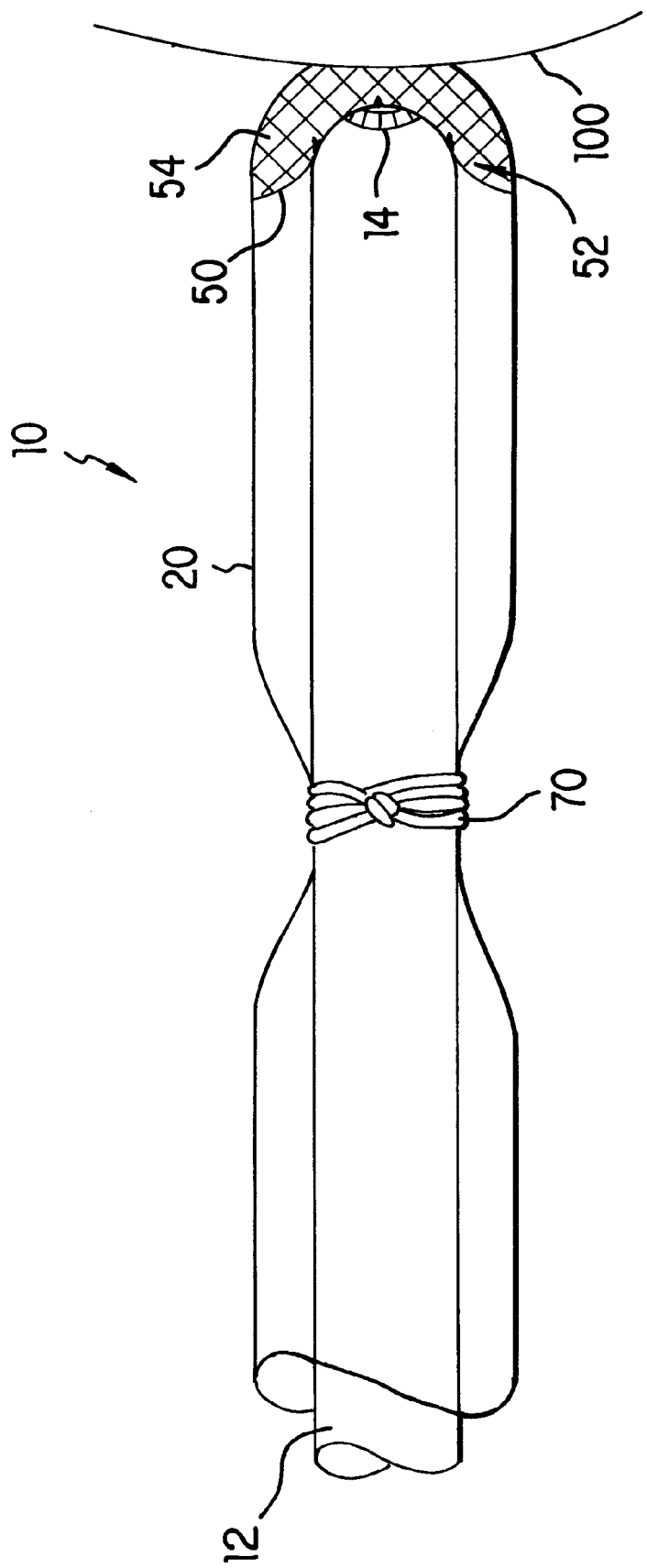
FIG. 2 is a side view, in partial cross-section, of the probe cover of FIG. 1, having a probe inserted into the cover for scanning a target body.

Referring now to FIGS. 1 and 2, in one preferred embodiment, the present invention comprises a probe cover 10 for covering at least a portion of an ultrasonic imaging probe 12. The ultrasonic imaging probe 12 is typically of a variety having at least one ultrasonic transducer 14, also referred to as an ultrasonic crystal. The probe will typically be of a type having a distal or free end or tip, and a proximal or connected end comprising a cord or other connection means for transmitting power and information between the probe and a separate base unit having a power source and a display. In preferred form, the probe cover 10 comprises a hollow body portion 20 forming a generally cylindrical flexible sheath having an interior surface 22 and an exterior surface 24. The interior of the body portion 20 defines a chamber 26 for receiving the ultrasonic imaging probe 12, or at least a portion of the probe 12 including the transducer 14. The flexible sheath formed by the body portion 20 generally comprises a first end 30 including an opening 32, communicating with the chamber 26, for receiving the probe 12, and a second end 34, generally opposite the first end 30, comprising a closed tip 36.

The probe cover 10 of the present invention preferably further comprises a deformable membrane 50 forming a reservoir 52 for containing a quantity of ultrasonically transmissive medium 54 such as ultrasonic imaging gel or non-toxic paraffin oil. The deformable membrane 50 is preferably attached to the interior surface 22, bounding the chamber 26 opposite the opening 32. In the embodiment of the probe cover 10 shown in the drawing figures, the reservoir 52 for containing the ultrasonically transmissive medium 54 is generally oriented adjacent the closed tip 36 at the second end 34 of the probe cover 10. It will be understood, however, that one or more reservoirs 52 can be provided at different locations on the probe cover 10, as needed to maintain ultrasonic contact between the probe cover 10 and one or more transducer portions 14 which may be located at various positions on different configurations of the probe 12.

As seen best by a comparison of FIGS. 1 and 2, the deformable membrane 50 of the present invention is preferably deformable between an undeformed position as shown in FIG. 1, and a deformed position as shown in FIG. 2. In the undeformed position, the reservoir 52 formed by the deformable membrane 50 comprises a first volume sufficient to contain a first quantity of ultrasonically transmissive medium. Upon contact by the probe 12, the deformable membrane 50 deforms into its deformed position shown in FIG. 2, wherein the reservoir 52 has a second volume, smaller than the first volume, and therefore sufficient to contain a smaller second quantity of ultrasonically transmissive medium. The deformable membrane deforms, rather than rupturing, thereby maintaining the integrity of the reservoir 52 throughout the use of the probe cover 10, and keeping the second quantity of ultrasonically transmissive medium in the desired position relative to the probe 12.

One or more vents or passages 60 are provided in the deformable membrane 50, to allow a portion of the ultrasonically transmissive medium 54 to flow or pass through the deformable membrane 50 upon deformation into its deformed position. The quantity of ultrasonically transmissive medium which will flow through the passage or passages 60 corresponds to a difference in volume, as defined by the first volume of the reservoir 52 when the deformable membrane 50 is undeformed, less the second volume of the reservoir 52 when the membrane 50 is deformed. The one or more passages 60 can comprise slits or perforations in the deformable membrane 50 which are closed to passage of the ultrasonically transmissive medium 54 when the deformable membrane 50 is in its undeformed position. When the deformable membrane 50 is deformed by contact from the probe 12, the one or more passages 60 are opened to allow passage of the ultrasonically transmissive medium 54. The selective opening of the one or more passages 60 can be achieved by, for example, forming the passages as perforations in the deformable membrane 50, or by using an overlapping seal. The one or more passages 60 can also comprise pores in a porous membrane material forming the deformable membrane 50. The size of the passages can be selected, for example, so that the ultrasonically transmissive medium 54 does not readily pass therethrough when the membrane 50 is undeformed, and upon deformation by contact from the probe 12 the membrane stretches, causing the size of the passages to increase to a size which allows the ultrasonically transmissive medium 54 to freely pass therethrough By appropriately selecting the first volume of the reservoir 52, and by controlling the extent of deformation of the deformable membrane 50 when the probe 12 is inserted in place within the probe cover 10, the second quantity of ultrasonically transmissive medium retained in the reservoir 52 can be controlled such that neither too much nor too little of the ultrasonically transmissive medium is retained in the area surrounding the transducer 14. This can be accomplished by the appropriate selection of the thickness and material of construction of the deformable membrane 50 to produce the desired stiffness or resistance to deformation, and/or by selective placement of the deformable membrane 50 within the chamber 26. This assures good ultrasonic contact between the probe cover 10 and the targeted body 100, and minimizes or eliminates potential reverberation artifacts. The quantity of ultrasonically transmissive medium 54 which flows through the passages 60 upon deformation of the deformable membrane 50, and into contact with the probe 12, is also selectively controlled in this manner to assure ultrasonic contact between the probe 12 and the probe cover 10. The extent of deformation of the deformable membrane 50 can be controlled by selective variation of the flexibility (i.e., the resistance to deformation) of the membrane 50, by varying the location of attachment of the membrane 50 on the interior wall 22 of the cover 10, and/or by control of the placement of the probe 12 within the cover 10.

Figure 3:
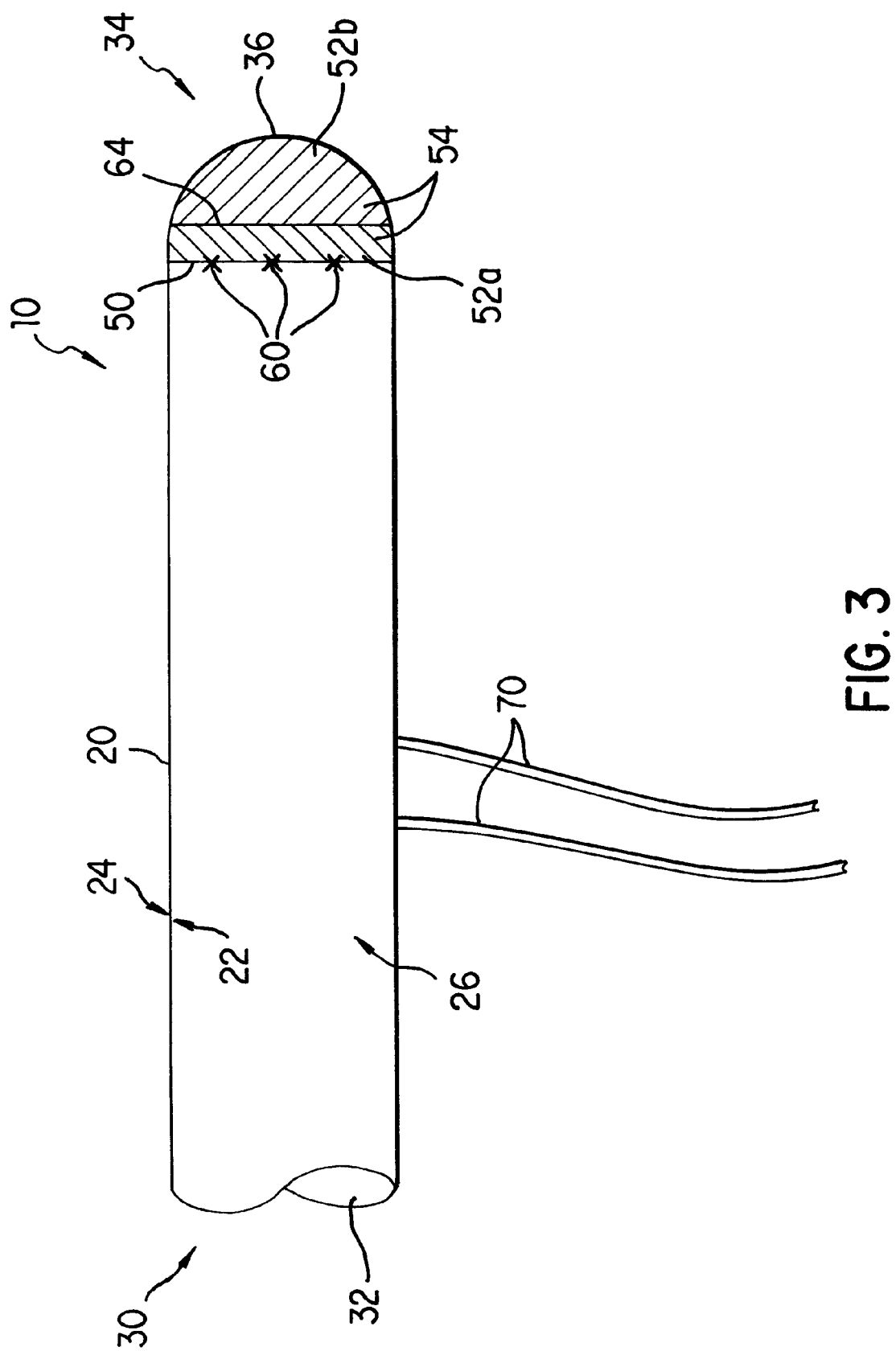
FIG. 3 is a side view, in partial cross-section, of a probe cover according to another form of the present invention.
Figure 4:
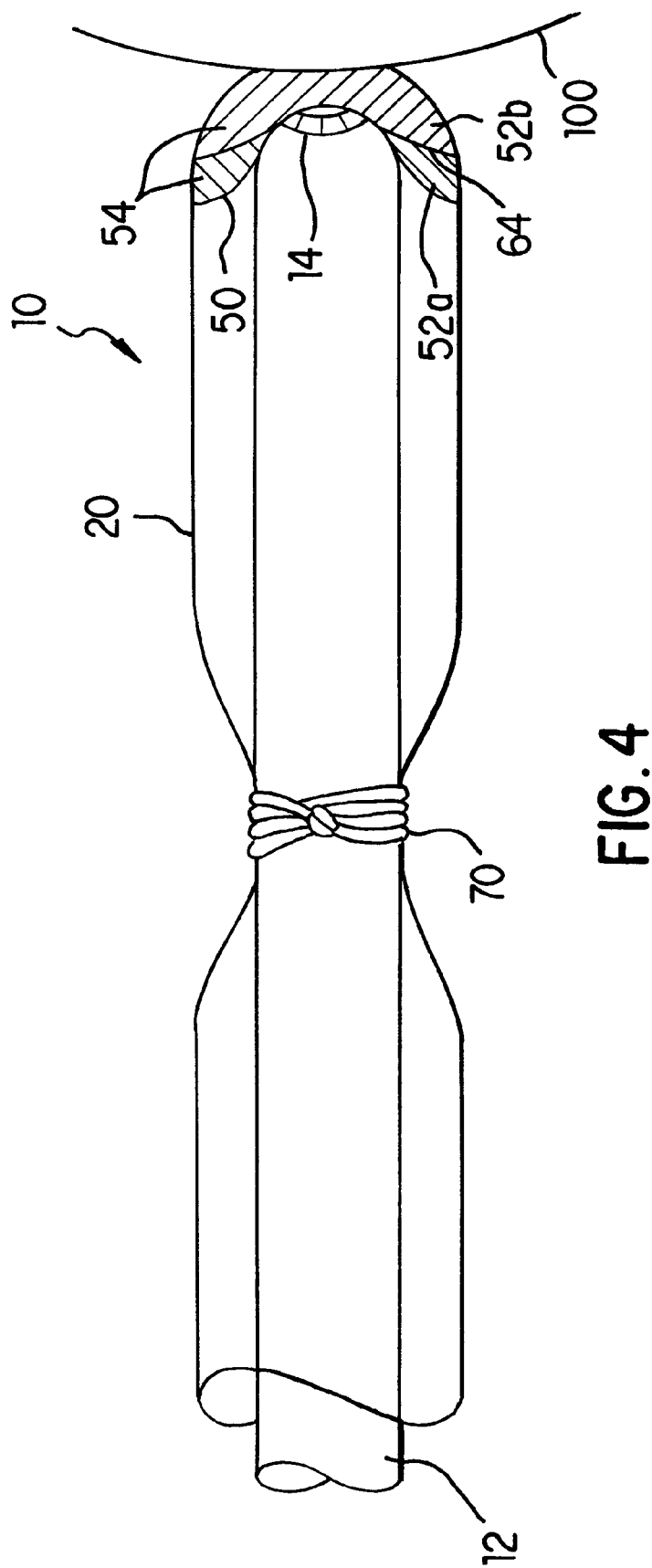
FIG. 4 is a side view, in partial cross-section, of the probe cover of FIG. 3, having a probe inserted into the cover for scanning a target body.

Another preferred embodiment of the present invention is best understood with reference to FIGS. 3 and 4. As depicted, this embodiment of the probe cover 10, as well as its method of use, is substantially as described herein with reference to FIGS. 1 and 2, with the addition of an impermeable membrane 64 between the deformable membrane 50 and the tip 36. The impermeable membrane 64 can be attached to the interior surface 22 of the wall portion 20, or can be attached to the deformable membrane 50. The impermeable membrane 64 is formed from a flexible material which does not permit passage of the ultrasonically transmissive medium 54 therethrough, thereby segregating the reservoir 52 into a dispensing chamber 52a and a non-dispensing chamber 52b. By appropriately selecting the placement of the deformable membrane 50 and the impermeable membrane 64 within the chamber 26, the volumes of the dispensing chamber 52a and the non-dispensing chamber 52b, and thereby the quantity of ultrasonically transmissive medium 54 contained in chambers 52a, 52b can be selectively controlled. Upon insertion of the probe 12 into the probe cover 10, the probe 12 contacts and deforms the deformable membrane 50 to expel at least a portion of the ultrasonically transmissive medium 54 from the dispensing chamber 52a, through the one or more passages 60, into the chamber 26 and into contact with the transducer portion 14 of the probe 12. The impermeable membrane 64 does not release any of the quantity of ultrasonically transmissive medium 54 contained within the non-dispensing chamber 52b, and thereby serves to constrain this quantity of ultrasonically transmissive medium 54 in place over the transducer portion 14 of the probe 12.

The probe cover 10 of the present invention can be formed from any flexible elastomeric material. For example, the body portion 20 which forms the generally cylindrical flexible sheath of probe cover 10 can be fabricated from a latex rubber material, or from a polyethylene material. Similarly, the deformable membrane 50 of the probe cover 10 can be formed from any flexible material of sufficient toughness and resiliency to withstand deformation from contact with the ultrasonic imaging probe 12, without rupturing. For example, the deformable membrane 50 can also be fabricated from materials including latex rubber and polyethylene.

The probe cover 10 of the present invention can further comprise one or more securing means such as tie elements 70, for releasably attaching the probe cover 10 to the probe 12. The tie elements 70 are preferably attached to the exterior surface 24 of the flexible sheath of the probe cover 10. Alternatively, the tie elements 70 can be integrally formed with the body portion 20 of the probe cover 10. Preferably, two separate tie elements 70 are provided, each having one end attached to the exterior surface 24 of the body portion 20. Alternatively, a single tie element can be provided, having its middle portion attached to the body portion 20 and having two free ends extending therefrom. The tie elements 70 are preferably fabricated from the same material of construction as the body portion 20 of the probe cover 10. For example, the tie elements 70 can be formed from latex rubber or polyethylene. The tie elements 70 are of a width and thickness sufficient to securely retain the probe cover 10 in place on the probe 12. The tie elements 70 are of a length sufficient to permit the tie elements 70 to be wrapped about the exterior 24 of the probe cover 10 when the probe 12 is inserted in place therein, substantially as shown in FIG. 2. Alternate embodiments of the probe cover 10 may comprise other types of securing means, such as elastically resilient sections of the probe cover 10, releasable adhesives, straps, or other fasteners.

In operation, the probe cover of the present invention enables a method of covering an ultrasonic imaging probe 12 with a flexible probe cover 10. The method enabled by present invention can best be described with reference to FIGS. 1 and 2. A probe cover 10, substantially as described above, includes an opening 32 for receiving the probe 12. At least the transducer portion 14 of the probe 12 is inserted into the chamber 26 of the probe cover 10, to bring the transducer portion 14 of the probe 12 into contact with the deformable membrane 50. The deformable membrane 50 is deformed into its deformed position, shown in FIG. 2, from the contact with the probe 12. The probe cover 10 can then be tied in place on the probe 12 by wrapping element 70 about the exterior surface 24 of the probe cover 10, to secure the interior surface 22 of the probe cover 10 against the probe 12. The tie element 70 can then be tied off to hold the probe cover 10 in position relative to the probe 12 throughout the examination of the targeted body 100.

The deformation of the deformable membrane from its undeformed position into its deformed position preferably opens the one or more passages 60 to permit flow of the ultrasonically transmissive medium 54 therethrough. Because the second volume of the reservoir 52, which corresponds to the deformed position of the deformable membrane 50, is smaller than the initial or first volume of the reservoir 52, corresponding to the undeformed position of membrane 50, an amount of ultrasonically transmissive medium is expelled from the reservoir 52 through the passage 60 upon deformation of the deformable membrane 50 by contact from the probe 12. This quantity of ultrasonically transmissive medium corresponds to the difference in volume between the first and second volumes of the reservoir 52. As this amount of ultrasonically transmissive medium flows through the passages 60, it preferably contacts the probe 12 adjacent its transducer portion 14, thereby ensuring ultrasonic contact between the probe 12 and the probe cover 10. The remainder of the ultrasonically transmissive medium 54 is retained within the reservoir 52 to ensure ultrasonic contact between the targeted body 100 and the probe cover 10 throughout the examination.

The above described embodiments are given as illustrative examples only. It will be readily appreciated that many deviations may be made from the specific embodiments disclosed in this specification without departing from the invention. Accordingly, the scope of the invention is to be determined by the claims below rather than being limited to the specifically described embodiments above.

What is claimed is:

1. A probe cover for covering at least a transducer portion of an ultrasonic imaging probe, said probe cover comprising:

(a) a hollow body portion having an interior surface and an exterior surface, said interior surface defining a chamber for receiving at least a portion of an ultrasonic imaging probe, said hollow body portion defining an opening therethrough communicating with said chamber; and (b) a deformable membrane within said hollow body portion adjacent said chamber, said deformable membrane bounding a reservoir for containing a quantity of ultrasonically transmissive medium, said deformable membrane defining at least one passage therethrough, the at least one passage allowing a portion of the quantity of ultrasonically transmissive medium to pass through said deformable membrane, from the reservoir to the chamber, upon deformation of said deformable membrane.

2. The probe cover of claim 1, wherein said deformable membrane comprises a porous membrane and each said at least one passage comprises a pore in said porous membrane.

3. The probe cover of claim 1, wherein said deformable membrane is flexible between an undeformed position wherein the reservoir has a first volume sufficient to contain a first quantity of ultrasonically transmissive medium, and a deformed position wherein the reservoir has a second volume smaller than the first volume.

4. The probe cover of claim 3, wherein a difference in volume is defined by the first volume less the second volume, the difference in volume corresponding to an amount of ultrasonically transmissive medium sufficient to maintain ultrasonic contact between the ultrasonic imaging probe and said probe cover.

5. The probe cover of claim 3, wherein the deformable membrane defines a slit comprising the at least one passage, the slit being closed to passage of the ultrasonically transmissive medium when said deformable membrane is in its undeformed position and open to passage of the ultrasonically transmissive medium when said deformable membrane is in its deformed position.

6. The probe cover of claim 3, wherein each said at least one passage has an opening size selected to prevent passage of the ultrasonically transmissive medium therethrough when said deformable membrane is in its undeformed position, and to allow passage of the ultrasonically transmissive medium therethrough when said deformable membrane is in its deformed position.

7. The probe cover of claim 3, wherein the second volume retains an amount of ultrasonically transmissive medium in the reservoir sufficient to maintain ultrasonic contact between the ultrasonic imaging probe and a targeted body.

8. The probe cover of claim 7, wherein said hollow body portion comprises a flexible sheath having a first end comprising said opening and a second end comprising a closed tip, said deformable membrane being attached to said interior surface adjacent the closed tip, and said chamber extending between the opening and said deformable membrane.

9. The probe cover of claim 8, wherein said hollow body portion comprises a material selected from the group consisting of latex rubber and polyethylene, and wherein said deformable membrane comprises a material selected from the group consisting of latex rubber and polyethylene.

10. The probe cover of claim 1, further comprising at least one securing means for affixing said probe cover to an ultrasonic imaging probe.

11. The probe cover of claim 10, wherein said at least one securing means is formed from the same material as said hollow body portion.

12. The probe cover of claim 1, wherein said deformable membrane is attached to said interior surface at a position whereby the transducer portion of an ultrasonic imaging probe contacts and deforms said deformable membrane when a probe is in place within said chamber.

13. The probe cover of claim 1, further comprising an impermeable membrane segregating said reservoir into a dispensing chamber and a non-dispensing chamber.

14. A probe cover for covering at least a transducer portion of an ultrasonic imaging probe, said probe cover comprising:
 (a) a flexible sheath defining a chamber therein for receiving at least the transducer portion of an ultrasonic imaging probe; and
 (b) a reservoir within said flexible sheath, segregated from said chamber by a deformable membrane having at least one passage therethrough, said reservoir containing a quantity of ultrasonically transmissive medium.

15. The probe cover of claim 14, further comprising securing means for attaching said probe cover to an ultrasonic imaging probe.

16. The probe cover of claim 14, wherein said deformable membrane comprises at least one passage therethrough said passage allowing fluid communication between said reservoir and said chamber.

17. The probe cover of claim 16, wherein said deformable membrane is deformable upon contact with the transducer portion of an ultrasonic imaging probe between an undeformed position wherein the reservoir has a first volume sufficient to contain a first quantity of ultrasonically transmissive medium, and a deformed position wherein the reservoir has a second volume sufficient to contain a second quantity of ultrasonically transmissive medium.

18. The probe cover of claim 17, wherein the second quantity of ultrasonically transmissive medium is sufficient to maintain ultrasonic contact between said probe cover and a targeted body, and wherein a difference in volume is defined by the first volume less the second volume, the difference in volume corresponding to an amount of ultrasonically transmissive medium sufficient to maintain ultrasonic contact between the transducer portion of the ultrasonic imaging probe and said probe cover.

19. The probe cover of claim 16, wherein the at least one passage is closed to passage of the ultrasonically transmissive medium when said deformable membrane is in its undeformed position and open to passage of the ultrasonically transmissive medium when said deformable membrane is in its deformed position.

20. The probe cover of claim 16, wherein said flexible sheath comprises a material elected from the group consisting of latex rubber and polyethylene, and wherein said deformable membrane comprises a material selected from the group consisting of latex rubber and polyethylene.

21. A method of covering an ultrasonic imaging probe with a flexible probe cover, the probe cover having a chamber for receiving a portion of the probe, a reservoir for containing a quantity of ultrasonically transmissive medium, and a deformable membrane between the chamber and the reservoir, said method comprising:
 (a) inserting at least a portion of the ultrasonic imaging probe into the chamber;
 (b) contacting the ultrasonic imaging probe with the deformable membrane; and
 (c) deforming the deformable membrane due to the contact with the ultrasonic imaging probe so as to cause a portion of the quantity of ultrasonically transmissive medium to pass through the deformable membrane, from the reservoir to the chamber, and into ultrasonic contact with the ultrasonic imaging probe.

22. The method of claim 21, wherein the deformable membrane is initially closed to passage of the ultrasonically transmissive medium, and wherein the method further comprises opening at least one passage through the deformable membrane upon contact with the ultrasonic imaging probe to allow transmission of the ultrasonically transmissive medium from the reservoir to the chamber.

23. The method of claim 21, wherein the probe cover includes securing means for attaching the probe cover to the probe, and wherein the method further comprises attaching the probe cover to the ultrasonic imaging probe with the securing means.

24. A probe cover for covering at least a transducer portion of an ultrasonic imaging probe, said probe cover comprising:
 (a) a hollow body portion having an interior surface and an exterior surface, said interior surface defining a chamber for receiving at least a portion of an ultrasonic imaging probe, said hollow body portion defining an opening therethrough communicating with said chamber;
 (b) a deformable membrane within said hollow body portion adjacent said chamber, said deformable membrane bounding a reservoir for containing a quantity of ultrasonically transmissive medium, said deformable membrane defining at least one passage therethrough, the at least one passage allowing a portion of the quantity of ultrasonically transmissive medium to pass through said deformable membrane upon deformation of said deformable membrane; and
 (c) an impermeable membrane segregating said reservoir into a dispensing chamber and a non-dispensing chamber.

25. The probe cover of claim 24, wherein the at least one passage through the deformable membrane is closed to passage of the ultrasonically transmissive medium when said deformable membrane is in an undeformed position and open to passage of the ultrasonically transmissive medium when said deformable membrane is in a deformed position.

* * * * *